United States Patent [19]

Ardecky et al.

[11] Patent Number: 5,091,390
[45] Date of Patent: Feb. 25, 1992

[54] TREATMENT OF CNS DISORDERS WITH 4,5,6,7-TETRAHYDRO-1H-IMIDAZO (4,5-)-PYRIDINES AND ANALOGS

[75] Inventors: Robert J. Ardecky; Andrew T. Chiu, both of Landenberg, Pa.; John J. V. Duncia, Newark, Del.; Petrus B. M. W. M. Timmermans, Kennett Square, Pa.; Ruth R. Wexler, Wilmington, Del.

[73] Assignee: E. I. du Pont de Nemours and Company, Wilmington, Del.

[21] Appl. No.: 585,422

[22] Filed: Sep. 20, 1990

[51] Int. Cl.$^5$ .................. A61K 31/435; C07D 471/04
[52] U.S. Cl. .................. 514/303; 514/215; 540/578; 546/118
[58] Field of Search .......... 540/578; 546/118; 548/252, 253, 254, 323; 514/215, 303, 381, 393

[56] References Cited

U.S. PATENT DOCUMENTS 4,812,462  3/1989  Blankley et al. .................. 546/118

FOREIGN PATENT DOCUMENTS

| | | |
|---|---|---|
| 0253310 | 7/1987 | European Pat. Off. |
| 0288907 | 4/1988 | European Pat. Off. |
| 0324377 | 1/1989 | European Pat. Off. |
| 307872 | 3/1989 | European Pat. Off. |
| 0399731 | 5/1990 | European Pat. Off. |
| 0400974 | 5/1990 | European Pat. Off. |

OTHER PUBLICATIONS

John M. Morgan, "Angiotensin Injected into the Neostriatum After Learning Disrupts Retention Performance" Apr. 1977, pp. 87–89 Science vol. 196.
B. A. Scholkens, W. Jung, W. Rascher, R. Dietz and D Ganten, "Intracerebroventricular angiotensin II increases arterial blood pressure in rhesus monkeys by stimulation of pituitary hormones and the sympathetic nervous system", Jul. 15, 1981, pp. 469–470.
Steven Whitebread, Michele Mele, Bruno Kamber and Marc de Gasparo, "Preliminary Biochemical Characterization of Two Angiotensin II Receptor Subtypes", Aug. 1989, pp. 284–291, Biochemical and Biophysical Research Communications.
James P. Bennett, Jr. and Solomon H. Snyder, "Angiotensin II Binding to Mammalian Brain Membranes", Dec. 1976, pp. 7423–7430, The Journal Of Biological Chemistry, vol. 251, No. 23.
Chiu et al., "Identification of Angiotensin II Receptor Subtypes", Nov. 1989, pp. 196–203, Biochemical and Biophysical Research Communications, vol. 165, No. 1.
Barnes et al., "Angiotensin II inhibits the release of [$^3$H] acetylcholine from rat entorhinal cortex in vitro", 1989, pp. 136–143.
Costall et al., "The Effects of ACE Inhibitors Captopril and SQ29,852 in Rodent Tests of Cognition", 1989, pp. 573–579.
Usinger et al., "Indications on the Memory-Enhancing Effects of a Peptidase Inhibitor", 1988, pp. 315–324.
Arregui et al., "Angiotensin Converting Enzyme in Alzheimer's Disease Increased Activity in Caudate Nucleus and Cortical Areas", 1982, pp. 1490–1492, Journal of Neuro Chemistry.
Koller et al., "Endogenous Brain Angiotensin II Disrupts Passive Avoidance Behavior In Rats", 1979, pp. 71–75.
Unger et al., "Brain angiotensin: pathways and pharmacology", 1988, pp. 140–154.
J. F. E. Mann, "Brain Angiotensin II Receptors: Possible Physiological Implications", 1982, pp. 242–254.
James T. Fitzsimons, "Angiotensin Stimulation of the Central Nervous System", 1980, pp. 117–167, Rev. Physiol. Biochem. Pharmacol., vol. 87.
Zubenko et al., "Cerebrospinal Fluid Levels of Angiotensin-Converting Enzyme, Acetylcholinesterase, and Dopamine Metabolites in Dementia Associated with Alzheimer's Disease and Parkinson's Disease; A Correlative Study", 1986, pp. 1365–1381.
Koller et al., "Endogenous Brain Angiotensin II Disrupts Passive Avoidance Behavior In Rats", 1979, pp. 71–75.

*Primary Examiner*—Bernard Dentz

[57] ABSTRACT

Provided are 4,5,6,7-tetrahydro-1H-imidazo(4,5-c)-pyridine derivatives, methods for preparing them, pharmaceutical compositions containing them, and methods of using them to treat disorders of mammals mediated by AII type-2 receptors in the central nervous system.

24 Claims, No Drawings

TREATMENT OF CNS DISORDERS WITH 4,5,6,7-TETRAHYDRO-1H-IMIDAZO (4,5-)-PYRIDINES AND ANALOGS

FIELD OF THE INVENTION

This invention relates to specific inhibitors of angiotensin II (AII) binding to angiotensin-II subtype-2 receptors.

BACKGROUND OF THE INVENTION

Angiotensin II (AII) is an octapeptide hormone which is a component of the renin-angiotensin system. In addition to being a circulating hormone which affects the cardiovascular system, the adrenal cortex, the peripheral autonomic nervous system, and the kidneys, AII is also known to affect the central nervous system. AII is now believed to act as a neuropeptide in the central nervous system (CNS) and may modulate the release and subsequent action of other neurotransmitters (Unger et al. (1988) *Circulation* 77 (Suppl I): 40-54).

Specific high affinity receptors for AII have been identified and localized in different regions of the CNS (Mann (1982) *Exp. Brain Res.* 4 (Suppl): 242). Stimulation of AII receptors in the CNS elicits a complex, but highly reproducible and concerted pattern of behavioral, cardiovascular, and endocrine responses (Fritzsimons (1980) *Rev. Physiol. Biochem. Pharmacol.* 87:117). These include CNS-induced elevation of blood pressure, increased drinking and sodium appetite, and release of antidiuretic hormone, oxytocin, luteinizing hormone, and prolactin (Scholken et al. (1982) *Experientia* 38:469). The CNS effects of AII could lead to hypertension and other cardiovascular diseases through inhibition of the baroreceptor reflex, increase in salt consumption, volume expansion, and increased peripheral resistance. Besides the cardiovascular system, AII may also influence the reproductive system and other brain functions, such as memory (Koller et al. (1975) *Neuroscience Lett.* 14: 71-75).

The major functions of AII in the CNS can be classified into three groups which may share, at least in part, overlapping mechanisms of action. The first major function of AII in the CNS is regulation of body fluid volume in response to hypovolemia, involving, for example, regulation of thirst, blood pressure increases, vasopressin release, sodium appetite increase, adrenocorticotropic hormone (ACTH) release, and aldosterone release (Unger et al. (1988) *Circulation* 77 (Suppl I): 40-54, and references cited therein). This CNS function of AII is closely related to the peripheral role of AII in hypertension.

A second function of AII in the CNS, although less well defined, is the regulation of gonadotrophic hormone releasing hormones and pituitary hormones during the reproductive cycle and pregnancy (Unger et al., supra).

A third possible CNS function of AII is a synaptic function. AII appears to interact with neurotransmitters such as acetylcholine (ACh), catecholamines, serotonin, and other neuroactive peptides (Unger et al., supra). Although the amount of data supporting this CNS function of AII is limited, published results suggest that increased AII activity in the brain exerts an inhibitory effect on cholinergic neurons resulting in impaired cognitive performance. Therefore, compounds that inhibit AII biosynthesis, or block AII receptor activation may enhance cognition.

The role of peptides in learning and memory was initially investigated by D. DeWied in the late 1960's and early 1970's. This led Morgan and Routtenberg (*Science* (1977) 196: 87-89) to investigate the role of AII in mediating retention of a passive avoidance (PA) response in rats. These authors demonstrated that rats injected with AII into the dorsal neostriatum, a brain area that has a high concentration of AII as well as precursors and metabolic enzymes for AII biosynthesis, showed a disruption in retention of a PA response. The authors demonstrated specificity of the response in terms of both the location in the brain, and the peptide used (unlike AII, thyrotropin releasing hormone or lysine-8-vasopressin had no effect). This study showed that increased AII in the dorsal neostriatum results in a cognitive impairment which is most likely related to AII modulation of neuronal activity that is necessary for consolidation of newly acquired information.

A different approach for investigating the behavioral effects of AII in the CNS was taken by Koller et al. (*Neuroscience Letters*(1975) 14: 71-75). These authors injected renin into the lateral ventricle of the brain (IVT) and measured increases in AII in cerebrospinal fluid (CSF); AII levels increased from 40 to about 5000 fmol per mL. This increase in AII was accompanied by a disruption of avoidance learning. These results suggested that renin-stimulated biosynthesis of AII could disrupt memory. Administration into the IVT of the angiotensin-converting enzyme (ACE) inhibitor SQ 14225 (captopril) prior to the renin injection, prevented the renin-induced avoidance disruption. Applicants have also found that renin administered IVT produces a dose-related amnesia in a PA task, which is prevented by IVT administration of the ACE inhibitor captopril. These results suggest that increased AII levels in the brain lead to a disruption of learned avoidance. This amnesia can be achieved by direct administration into a discrete brain area of either AII or renin, an enzyme involved in endogenous AII biosynthesis.

In the literature on the neuropathology and neurochemistry of Alzheimer's disease (AD), there are two reports of altered levels of dipeptidyl carboxypeptidase (angiotensin-converting enzyme, ACE) in human CSF and brain tissue. Arrequi et al. (*J. Neurochemistry*(1982) 38: 1490-1492) found increased ACE activity in the hippocampus, parahippocampal gyrus, frontal cortex, and caudate nucleus in AD patients. Zubenko et al. (*Biol. Psych.*21: 1365-1385 (1986) found a correlation between levels of ACE in the CSF and the severity of AD. Whether the alterations in ACE cause the progression of dementia or are correlates of the disease progress remains unknown.

Recent evidence that inhibition of ACE can have a modulatory effect on learning and memory was reported by Usinger et al. (*Drug Dev. Research* 14: 315-324 (1988); also European Patent application, EP 307,872 to Hoechst, published Mar. 22, 1989).

Similar results were reported by Costall et al. (*Pharmacol. Biochem. Behav.* 33: 573-579 (1989)) using the ACE inhibitor captopril. These authors demonstrated that subchronic treatment with captopril increased the rate of acquisition of light/dark habituation performance. Further, anticholinergic scopolamine-induced disruption of performance in this test model was prevented by daily treatment with captopril.

The ACE inhibitor SQ 29852 has also been reported to provide protective effects on memory of (3) R³ is
(a) R¹⁴—(CH₂)$_x$— wherein x and R¹⁴ are, independently, as defined above,
(b) R¹⁴R¹³ CH(CH₂)$_y$— wherein y is zero, one, two, three, four or five, R¹⁴ is as defined above, and R¹³ is lower alkyl, cycloalkyl, naphthyl, phenyl unsubstituted or substituted with from one through five substituents, comprising alkyl, halo, tri-fluoromethyl, amino, N,N-lower dialkylamino, lower thioalkyl, lower alkylsulfonyl, or nitro;
(c) —COR⁵ wherein R⁵ is
(i) alkyl of from one to fifteen carbons, inclusive,
(ii)

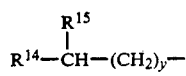

wherein R¹⁴ and y are, independently, as defined above, and R¹⁵ is H, lower alkyl, cycloalkyl, naphthyl, phenyl previously learned tasks and to ameliorate, at least in part, an anticholinergic effect on performance (European Patent application EP 288,907 to Squibb, published Nov. 2, 1988).

Evidence for a role of AII in cholinergic function was also reported by Barnes et al. (*Brain Research* 491: 136-143 (1989), who examined the effect of AII in an *in vitro* model of potassium stimulated release of [³H]ACh. AII, but not AI, reduced potassium-stimulated release of ACh without effects on basal levels. This effect was antagonized by the AII antagonist [1-sarcosine, 8-threonine]angiotensin II. These results suggest that AII can inhibit the release of ACh in the entorhinal cortex of rat brain.

The results summarized above suggest that increased AII activity in the brain may exert an inhibitory effect on cholinergic neurons, resulting in impaired cognitive performance. Thus, compounds that block AII receptor activation may enhance cognitive performance.

Carini and Duncia, U.S.S.N. 050,341, filed May 22, 1987, which is a continuation-in-part of U.S.S.N. 884,920, filed July 11, 1986, disclose angiotensin II receptor blocking imidazoles (also EP 0253 310, published 20.01.88, and EP 0324 377, published July 19, 1989).

Blankley et al., U.S. Pat. No. 4,812,462, issued Mar. 14, 1989, to Warner-Lambert, disclose 4,5,6,7-tetrahydroimidazo-[4,5-c]-pyridine derivatives, which are said to be useful for the treatment of hypertension.

SUMMARY OF THE INVENTION

According to the present invention, there are provided compounds of Formula I, pharmaceutical compositions containing them, and methods of using them to treat disorders mediated by AII receptors, including cognitive and learning disorders. Included are compounds of the formula:

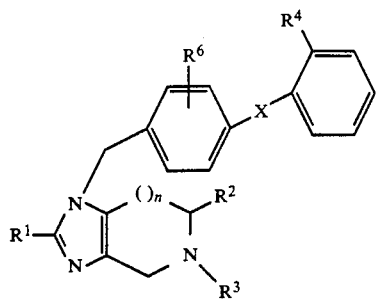

or a pharmaceutically acceptable salt thereof; wherein
(1) R¹ is:
(a) H,
(b) halo,
(c) C₁-C₆ alkyl, or C₃-C₆ alkenyl or alkynyl,
(d) R¹⁴-(CH₂)$_x$-wherein x is one, two, three, four or five, and R¹⁴ is C₃-C₈ cycloalkyl, naphthyl, heteroaryl, phenyl unsubstituted or substituted with from one through five, preferably one through three, substituents comprising C₁-C₄ alkyl, halo, trifluoromethyl, hydroxy, C₁-C₄ alkoxy, lower acyloxy, amino, N-lower monoalkylamino, N,N-lower dialkylamino, lower thioalkyl, lower alkylsulfonyl, nitro or -NHCOR¹⁰ wherein R¹⁰ is lower alkyl, phenyl unsubstituted or substituted with lower alkyl, or -NHR¹¹; wherein R¹¹ is H or C₁-C₄ alkyl,
(e)

wherein R¹⁴ is independently as defined above, or
(f) R¹⁴-CH(OH)- wherein R¹⁴ is independently as defined above;
(2) R² is
(a) —(CH₂)$_x$OR⁷ wherein R⁷ is H, C₁-C₄ alkyl, C₁-C₄ acyl, C₃-C₆ cycloalkyl, phenyl, or benzyl,
(b) —(CH₂)$_x$NR⁷R⁸ wherein R⁷ is independently as defined above and R⁸ is H, C₁-C₄ alkyl, phenyl, benzyl, or C₁-C₄ acyl
(c) —(CH₂)$_x$OCH₂R⁷ wherein R⁷ and x are as defined above,
(d) —CHO
(e) —CN,
(f) —COOR⁹ wherein R⁹ is hydrogen, C₁-C₄ alkyl or benzyl;
(3) R³ is
(a) R¹⁴-(CH₂)$_x$- wherein x and R¹⁴ are, independently, as defined above,
(b) R¹⁴R¹³CH(CH₂)$_y$- wherein y is zero, one, two, three, four or five, R¹⁴ is as defined above, and R¹³ is lower alkyl, cycloalkyl, naphthyl, phenyl unsubstituted or substituted with from one through five substituents, preferably from one through three substituents, comprising alkyl, halo, trifluoromethyl, amino, N-lower monoalkyl amino, N,N-lower dialkylamino, lower thioalkyl, lower alkylsulfonyl, or nitro;
(c) —COR⁵ wherein R⁵ is
(i) alkyl of from one to fifteen carbons, inclusive,
(ii)

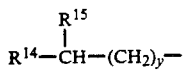

wherein $R^{14}$ and y are, independently, as defined above, and $R^{15}$ is H, lower alkyl, cycloalkyl, naphthyl, phenyl unsubstituted or substituted with from one through five substituents, preferably from one through three substituents, comprising alkyl, halo, trifluoromethyl, amino, N-lower monoalkylamino, N,N-lower dialkylamino, lower thioalkyl, lower alkylsulfonyl, OH, $C_1$-$C_4$ alkoxy, or nitro, (iii) —(CH=$CR^{12}$)-$R^{16}$, wherein $R^{12}$ is hydrogen or lower alkyl and $R^{16}$ is
  (a) alkyl of from four to twenty carbons, inclusive,
  (b)

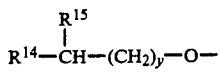

wherein y, $R^{14}$ and $R^{15}$ are, independently, as defined above, and (iv) $R^{14}(CH_2)_yR^{12}N$- wherein y, $R^{14}$ and $R^{12}$ are, independently, as defined above, (v) $R^{14}$-$(CH_2)_y$-O- wherein y and $R^{14}$ are independently as defined above, (vi)

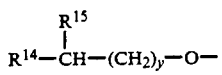

wherein $R^{14}$, $R^{15}$, and y are independently as defined above, (d) —$SO_2R^5$ wherein $R^5$ is, independently, as defined above, preferably $R^{14}$-$(CH_2)_y$-wherein $R^{14}$ and y are, independently, as defined above;

(4) $R^4$ is —$CO_2H$, —$NHSO_2CF_3$, or

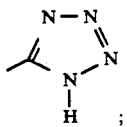

(5) $R^6$ is H, $C_1$-$C_4$ alkyl, halogen, phenyl, benzyl, or $C_1$-$C_4$ acyl;
(6) X is a carbon-carbon single bond, —NHCO—, —$OCH_2$—, —O—, or —CO—; and
(7) n=0-2.

Preferred are compounds of Formula I above wherein
$R^1$ is H, $C_1$-$C_6$ alkyl, $C_3$-$C_6$ alkenyl or alkynyl;
$R^2$ is —$(CH_2)_xOR^7$, —$(CH_2)_xNR^7R^8$, —CHO, —CN, —$CO2R^9$, —$(CH_2)_xOCH_2R^7$;
$R^3$ is —$COR^5$, —$(CH_2)xR^{14}$, —$(CH_2)yCHR^{13}R^{14}$, —$SO2(CH_2)_yR^{14}$;
R4 is —$CO_2H$, —$NHSO_2CF_3$, or

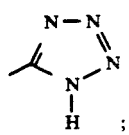

$R^5$ is $C_1$-$C_{10}$ alkyl, —$(CH_2)_yCHR^{14}R^{15}$, —O $(CH_2)_yR^{14}$, —O $(CH_2)_yCHR^{14}R^{15}$;
$R^6$ and $R^8$ independently are H, $C_1$-$C_4$ alkyl, phenyl, benzyl, or $C_1$-$C_4$ acyl;
$R^7$ is H, $C_1$-$C_4$ alkyl, $C_3$-$C_6$ cycloalkyl, phenyl, benzyl;
$R^{14}$ is $C_3$-$C_8$ cycloalkyl, naphthyl, pyridyl, furyl, thienyl, phenyl unsubstituted or substituted with 1-3 substitutents selected from $C_1$-$C_4$ alkyl, halogen, $CF_3$, OH, $C_1$-$C_4$ alkoxy, N-lower monoalkylamino, N,N-lower dialkylamino, or $NO_2$;
$R^{15}$ is H, $C_1$-$C_4$ alkyl, $C_3$-$C_8$ cycloalkyl, naphthyl, phenyl optionally substituted with 1-3 substitutents selected from $C_1$-$C_4$ alkyl, halogen, $CF_3$, OH, $C_1$-$C_4$ alkoxy, N-lower monoalkylamino, N,N-lower dialkylamino, or $NO_2$;
X is carbon-carbon single bond, —NHCO—, —$OCH_2$—, —O—, —CO—;
n=0-2;
x=1-5;
y=0-5.

More preferred are compounds of Formula I above wherein:
$R^3$ is $COR^5$;
$R^5$ is —$(CH_2)_yCHR^{14}R^{15}$;
n=1, 2.

Specifically preferred are the following compounds of Formula I: 1-[4-Amido-(2'-carboxyphenyl)-3-methylphenyl ]methyl-5-diphenylacetyl-4,5,6,7-tetrahydro-1H-imidazo (4,5-C)-pyridine-6-carboxylic acid, or a pharmaceutically acceptable salt thereof. Methyl-1-[4-amido-(2'-carboxyphenyl)-3-methylphenyl ]methyl-5-diphenylacetyl-4,5,6,7-tetrahydro-1H-imidazo (4,5-C)-pyridine-6-carboxylate, or a pharmaceutically acceptable salt thereof.

In compounds of the formula I, the term alkyl means from one to twenty carbons and one to fifteen carbons is meant to include a straight or branched alkyl group having the noted number of carbons, such as, for example, methyl, ethyl, propyl, butyl, pentyl, hexyl and the like and isomers thereof.

Halo includes particularly fluorine, chlorine or bromine.

Lower alkyl is methyl, ethyl, propyl, or butyl and isomers thereof.

Lower alkoxy is -0-alkyl wherein alkyl is lower alkyl.
Lower thioalkyl is -S-alkyl wherein alkyl is lower alkyl.

Lower acyloxy is alkyl

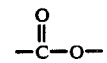

wherein alkyl is lower alkyl.
Lower alkylsulfonyl is alkyl

wherein alkyl is lower alkyl.

Heteroaryl is 2-, 3-, or 4-pyridyl; 1-, 2-, or 4-imidazolyl; 1-, 2-, 3-, 4-, 5-, 6- or 7-indolyl; 2-, or 3-thienyl; 2- or 3-furyl; or 1 -, 2-, or 3-pyrazolyl and the like.

Cycloalkyl is of from four to twenty carbons, inclusive, in a one, two or three saturated ring system, said ring comprising from four to eight carbons, inclusive, including monocyclic rings such as cyclobutyl, cyclopentyl, cyclohexyl and the like, or polycyclic rings such as adamantyl or norbornyl. Each ring may be unsubstituted or substituted by a straight or branched lower alkyl group.

DETAILED DESCRIPTION OF THE INVENTION

The new compounds of this invention may be obtained by the three following procedures:

Method A (Scheme 1).

A compound of formula 1 below, where Y is chloride, bromide, iodide, tosylate, mesylate, triflate, etc., and where X is a carbon-carbon single bond, —NHCO—, —OCH$_2$—, —O —, or —CO—and R$^4$ is —CO$_2$H, —NHSO$_2$CF$_3$, or tetrazole, is treated with the di-BOC histidine 2, at $-78°$ C. to give the benzylhistidine 3. Removal of the t-butoxycarbonyl (BOC) group of compound 3 with acid (HCl, etc.), followed by treatment of the intermediate with CH$_{2O}$, gives the imidazo(4,5-c)pyridine 4. The tetrahydropyridine 4 is not isolated but converted to the ester 5 by treatment with trialkyl orthoformate. Compound 5 is converted to 6 by treatment of the compound with dicyclohexylcarbodiimide (DCC), 1-hydroxybenzotriazole (HOBT), and an appropriate acid, or, alternatively,by treatment of Compound 5 with an alkyl halide, sulfonate or sulfonyl chloride. Hydrolysis of the ester group with dilute base (NaOH, etc.) followed by acid workup gives the acid (II) (R$^2$ =CO$_2$H) which can be converted to a compound of Formula I having the functional groups claimed for R$^{2,}$ by methods well known to one skilled in the art. For example, it is well-known to those skilled in the art to convert acids (R$^9$=H) to esters (R$^9$=C$_1$-C$_4$ alkyl or benzyl) simply by heating up the acid in the appropriate alcohol solvent with an appropriate acid catalyst (such as p-toluene sulfonic acid) and withdrawing the water formed as a by-product in the reaction using an apparatus such as a Dean-Stark trap.

Scheme 1

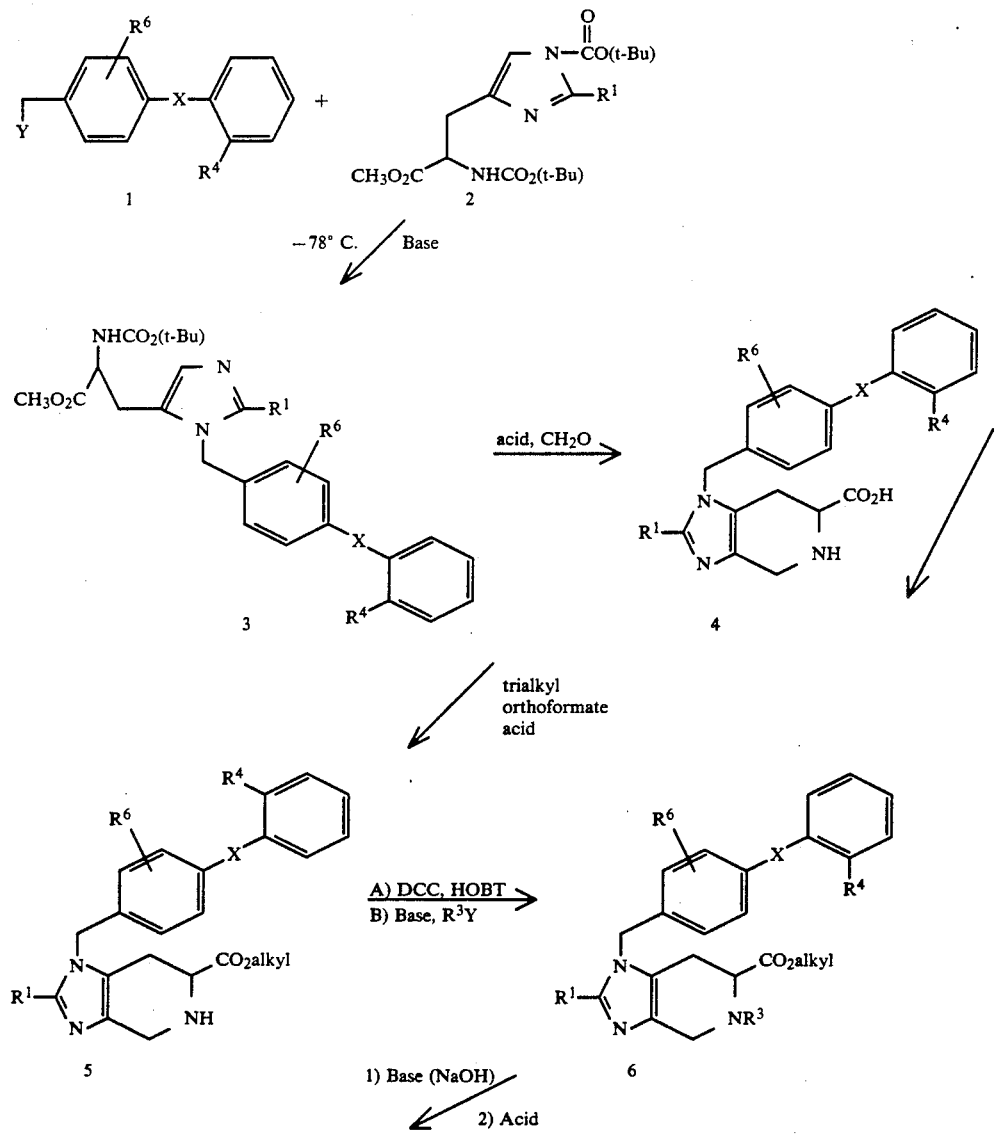

-continued
Scheme 1

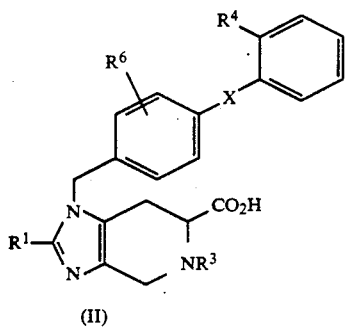

(II)

Method B (Scheme 2)

Compounds of the formula 1 are described in and prepared via the methods set froth in U.S. Pat. No. 4,812,462, issued Mar. 14, 1989, (European Patent application EPA 0 245 637, published Nov. 19, 1987), Warner-Lambert, the disclosures of which are hereby incorporated by reference.

Alkylation of 7 and separation of the isomers resulting therefrom is possible via treatment of 7 with an appropriate base such as sodium hydride or lithium diisopropylamide, followed by treatment of the anionic species with the appropriate halide or sulfonate 1 to give compounds of Formula (I) plus the regioisomer 8, which is separated from (I) via standard chromatographic techniques well known to one skilled in the art.

Scheme 2

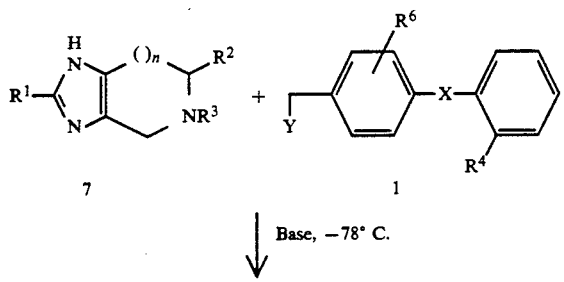

-continued
Scheme 2

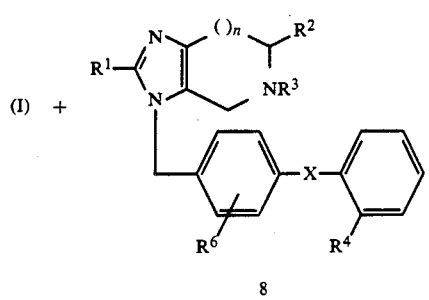

Method C (Scheme 3)

Compounds of the formulas 9–15 are prepared via the methods described in U.S. Pat. No. 4,812,462, the disclosures of which are hereby incorporated, by reference. Compounds of the Formula (I), where $R^2=CO_2H$ and, $X=NHCO$, may be prepared by reacting 15 with phthalic anhydride in a chlorinated solvent such as chloroform at room temperature for 24 hours.

Scheme 3

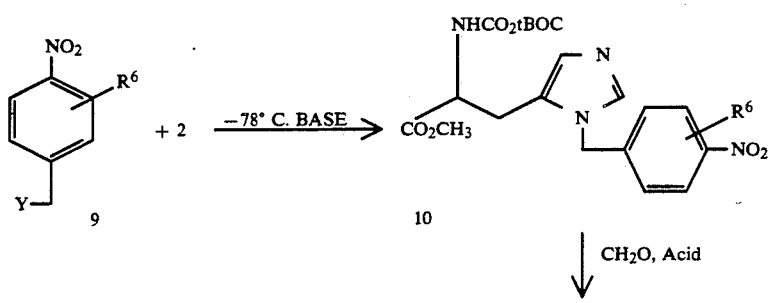

-continued
Scheme 3

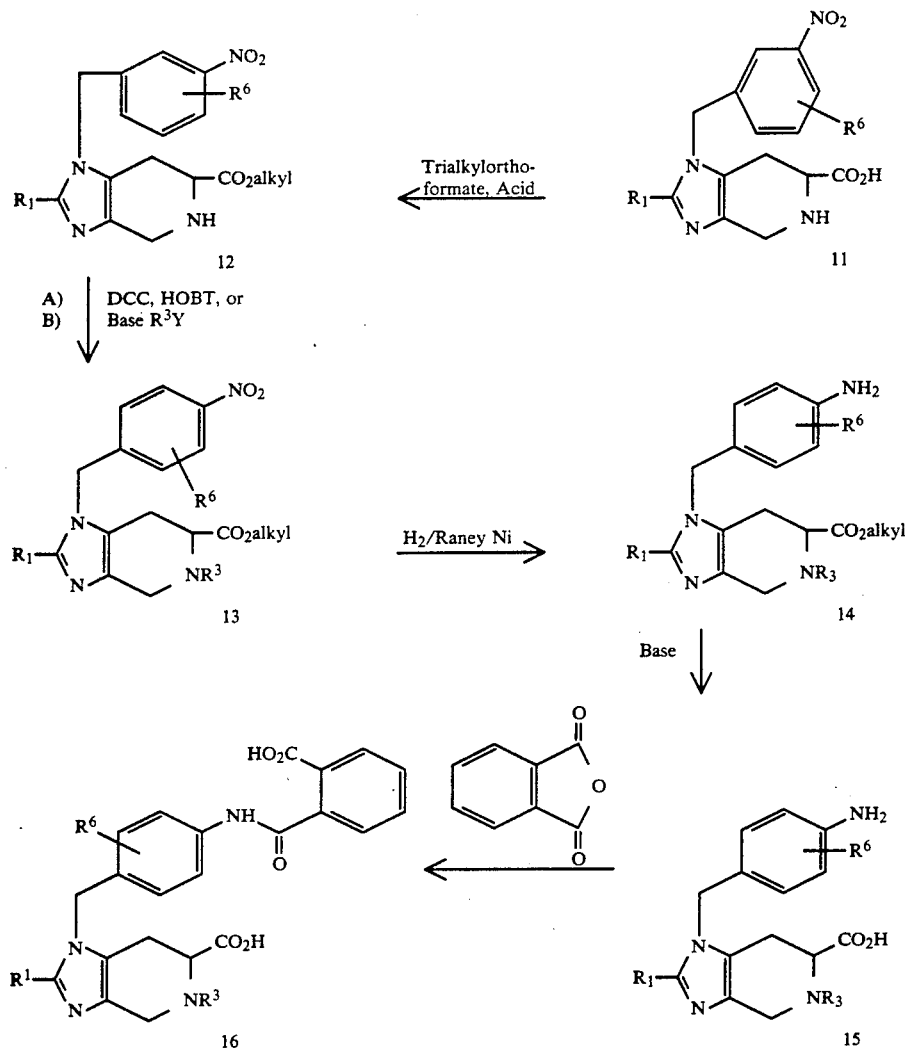

Preparation of Compound of Formula 10 of Scheme 3 Where

R⁶=3—CH₃

To 2.82 g of trifluoromethane sulfonic anhydride and 50 ml of dry methylene chloride at −78° C. is added slowly 1.67 g of compound 9 (3-bromomethyl-6-nitrotoluene, 10 mmole) 1.14 g of Et₃N (excess) in 10 ml of dry methylene chloride. The reaction was stirred for 30 min. at −78° C. and then a solution of 3.70 g (10 mmole) 2( di-boc-histidine, R¹=H), in 20 ml of dry methylene chloride was slowly added. The reaction is allowed to warm to room temperature overnight. To the reaction mixture was added 100 ml of pH 7 buffer and the mixture was stirred for 10 min. The organic layer was separated, dried and evaporated. The residue was chromatographed on silica gel using CH₂Cl₂/MeOH (80/20) to yield 1.40 g (33 %) of 10(1-methyl-6-nitrotoluene)-boc-histidine, NMR (CDCl₃) 7.98 (m, 2H), 7.49 (m, 1H), 7.14 (s, 1H), 7.02 (b, 1H), 5.75 (b, 1H), 5.19 (d, 2H), 4.51 (m, 1H), 3.72 (s, 3H), 2.57 (d, 2H), 2.55 (s, 3H), 2.25 (s, 3H), 1.42 (s, 9H).

Preparation of Compound of Formula 12 of Scheme 3, Where

R¹=H, R⁶=3—CH₃, alkyl=CH₃

A solution of 10.0 g (27 mmole) 10, where R⁶=3—CH₃) (prepared above) and 200 ml of 6acid was refluxed overnight. The reaction was cooled and evaporated under vacuum to yield a glass. This crude glass was dissolved in 200 ml of 1N HCl and then treated with 12.0 ml of 37 % formaldehyde solution and stirred for 1 hour at room temperature. This solution was then refluxed for 1.5 hours and then cooled and evaporated under vacuum to yield a glass. This crude glass was dissolved in 200 ml of methanol containing 20 ml (excess) trimethylorthoformate. This solution was refluxed while hydrochloric acid gas was bubbled in overnight. The reaction was cooled and evaporated under reduced pressure. The residue was dissolved in methylene chloride, washed 2 times with 50 ml of 10 % sodium carbonate solution, dried and evaporated. The residue was chromatographed using silica gel using CH₂Cl₂/MeOH (95/5) to yield 3.40 g (40 %) of the tetrahydropyridine 12(R¹=H, R⁶=3—CH₃, alkyl =CH3), NMR (DMSO- D6)d 7.96 (d, 1H), 7.64 (s, 1H), 7.05 (m, 2H), 5.23 (s, 2H), 3.62 (m, 4H), 3.54 (s, 3H), 2.78 (b,1H), 2.55 (s, 3H).

Preparation of Tetrahydropyridine Compound of Formula 13 Scheme 3, Where $R^1=H$, $R^6=3—CH_3$, $R^3=COCH(Ph)_2$, alkyl $=CH_3$ A) A solution of 2.03 g of dicyclohexylcarbodiimide (DCC), 2.03 g of hydroxybenzotriazole hydrate, 2.03 g of diphenylacetic acid and 50 ml of acetonitrile were stirred for 1 hour at room temperature. To this solution was added slowly a solution of 3.70 g (11.7 mmole) of the tetrahydropyridine 12 ($R^1=H$, $R^6=3—CH3$). The reaction was stirred for 72 hours at room temperature. The reaction was then filtered and the organic phase was evaporated under vacuum. The residue was dissolved in 300 ml of methylene chloride and washed with 100 mls of 10 % sodium carbonate solution and then the organic phase was dried and evaporated. The residue was chromatographed on silica gel using $CH_2Cl_2/MeOH$ (90/10) to yield 2.68 g ( 44 %) of the tetrahydropyridine 13 ($R^1=H$, $R^6=3—CH_3$, $R^3=CO(Ph)_2$, alkyl $=CH_3$), NMR (CDCl$_3$)d 7.94 (d, 1H), 7.44 (s, 1H), 7.30 (m, 10H), 7.00 (B, 2H), 6.01 (d, 2H), 4.88 (b, 2H), 4.45 (b, 2H), 3.59 (s, 3H), 3.44 (s, 1H), 2.77 (b,1H), 2.58 (s, 3H),, MP 91–97° C.

Preparation of Tetrahydropyridine of Formula 16, Where $R^1=H$, $R^3=COCH(Ph)2$, $R^6=3—CH_3$, X=4—NHCO, $R^432$ $CO_2H$ A solution of 1.0 g (1.9 mmole) of compound of formula 13 ($R^1=H$, $R^6=3—CH_3$, $R^3=COCH(Ph)_2$, Alkyl $=CH_3$), 120 ml of tetrahydrofuran, 60 ml of methanol and 2.0 g of Raney nickel was placed in a Parr shaker pressurized to 45 psi with hydrogen gas. The reaction was shaken for 48 hours and then carefully filtered through Celite (diatomaceous earth), washed with methylene chloride, and the combined organic phase was evaporated under vacuum to yield a oil. The oil was triturated with hexane to yield 0.83 g (88%). This solid was dissolved in 40 ml of methanol and stirred at room temperature while 1.69 ml of 1.000 N NaOH was slowly added. The mixture was stirred at room temperature for 12 hours and the solvents were removed under vacuum to yield 0.80 g of a white solid. This solid 0.80 g (2.7 mmole) was dissolved in 25 of dry tetrahydrofuran containing 0.41 g of phthalic anhydride (2.7 mmole) and refluxed for twelve hours and cooled. The resulting solution was acidified to pH 7 with 10% HCl and then the solvents were evaporated under vacuum to yield an off white solid, which was chromatographed on silica gel using methylene chloride/methanol 80/20 to yield 1.1 g (62%) of Tetrahydropyridine (16) ($R^1=H$, $R^3=COCH(Ph)_2$, $R^6=3—CH_3$, X=4—NC $R^4=CO_2H$), NMR (DMSO—D6)d 7.48 (s, 1H), 7.23 (m, 10H), 6.79 (m, 3H), 5.51 (s, 2H), 4.35—4.78 (m, 5H), 2.00 (s, 3H). MP=198-203° C.

The compounds of Table I were prepared or can be prepared by, Methods A, B and C above. This table is not meant to be limiting to the compounds which could be prepared of the scope of this invention.

TABLE I

| Ex | $R^1$ | $R^2$ | $R^3$ | X | $R^4$ | $R^6$ |
|---|---|---|---|---|---|---|
| 1 | H | $CO_2H$ | $COCH(Ph)_2$ | NHCO | $CO_2H$ | 3-$CH_3$ |
| 2 | H | $CO_2CH_3$ | $COCH(Ph)_2$ | NHCO | $CO_2H$ | 3-$CH_3$ |
| 3 | H | $CO_2H$ | $COCH(Ph)_2$ | $OCH_2$ | $CO_2H$ | 3-$CH_3$ |
| 4 | H | $CO_2CH_3$ | $COCH(Ph)_2$ | $OCH_2$ | tetrazole | 3-$CH_3$ |
| 5 | $C_4H_9$ | $CO_2H$ | $COCH(Ph)_2$ | O | $NHSO_2CF_3$ | 3-$C_6H_5$ |
| 6 | $C_5H_{11}$ | $CO_2CH_3$ | $COCH_3$ | O | $NHSO_2CF_3$ | 3-$C_6H_5$ |
| 7 | $C_2H_5$ | $CO_2H$ | $COCH(PH)_2$ | CO | $CO_2H$ | 3-$CH_2C_6H_5$ |
| 8 | $C_2H_5$ | $CO_2CH_3$ | $COC_3H_7$ | CO | tetrazole | 3-$CH_2C_6H_5$ |
| 9 | $C_3H_7$ | $CO_2H$ | $CH_2$-2-thienyl | single bond | $CO_2H$ | 3-$CH_3$ |
| 10 | $C_4H_9$ | $CO_2CH_3$ | $CH_2$-2-furyl | single bond | $CO_2H$ | 3-$CH_3$ |
| 11 | $CH_3$ | $CO_2H$ | $CH_2$-2-furyl | NHCO | tetrazole | 3-$C_3H_7$ |
| 12 | $CH_3$ | CN | $SO_2CH_2C_6H_5$ | NHCO | tetrazole | 3-$C_3H_7$ |
| 13 | $C_2H_5$ | $CO_2H$ | $SO_2CH_2C_6H_5$ | NHCO | tetrazole | 3-$C_4H_9$ |
| 14 | $C_2H_5$ | $CO_2CH_3$ | $SO_2CH_2$-2-naphthyl | NHCO | tetrazole | 3-$C_4H_9$ |
| 15 | $CH_3$ | $CH_2N(CH_3)_2$ | $SO_2CH_2$-naphthyl | $OCH_2$ | $CO_2H$ | 3-$COCH_3$ |
| 16 | $CH_3$ | $CH_2N(C_2H_5)_2$ | $COC_6H_{13}$ | $OCH_2$ | $CO_2H$ | 3-$COCH_3$ |
| 17 | $C_2H_5$ | CN | $COC_6H_{13}$ | $OCH_2$ | $CO_2H$ | H |
| 18 | $C_2H_5$ | $CO_2C_6H_5$ | $COCH(Ph)_2$ | $OCH_2$ | tetrazole | H |
| 19 | $CH_3$ | $CH_2OCH_3$ | $COCH(Ph)_2$ | single bond | tetrazole | 2-$CH_3$ |
| 20 | $CH_3$ | $CO_2CH_3$ | $COCH(Ph)_2$ | single bond | tetrazole | 3-$CH_3$ |
| 21 | $C_3H_7$ | $CO_2H$ | $COCH(Ph)_2$ | single bond | $NHSO_2CF_3$ | 3-$CH_3$ |
| 22 | $C_3H_7$ | CHO | $SO_2CH_2C_6H_5$ | single bond | $NHSO_2CF_3$ | H |
| 24 | H | $CO_2H$ | $COCH(Ph)_2$ | single bond | tetrazole | 3-$CH_3$ |
| 25 | H | $CO_2CH_3$ | $COCH(Ph)_2$ | single bond | tetrazole | 3-$CH_3$ |

TABLE I-continued

| | | | | | | |
|---|---|---|---|---|---|---|
| 26 | $C_3H_7$ | $CO_2H$ | $COCH(Ph)_2$ | single bond | tetrazole | 3-$CH_3$ |
| 27 | H | $CO_2H$ | $COCH(Ph)_2$ | single bond | tetrazole | H |
| 28 | $C_3H_7$ | $CO_2H$ | $COCH(Ph)_2$ | single bond | tetrazole | H |
| 29 | H | $CO_2CH_3$ | $COCH(Ph)_2$ | single bond | tetrazole | 2-Br |
| 30 | $C_4H_9$ | $CO_2H$ | $COCH(Ph-4Cl)_2$ | O | $NHSO_2CF_3$ | 3-$C_6H_5$ |
| 31 | $C_5H_{11}$ | $CO_2CH_3$ | $CONCH_3(Ph)$ | O | $NHSO_2CF_3$ | 3-$C_6H_5$ |
| 32 | $C_2H_3$ | $CO_2H$ | $CONCH_3(Ph)$ | CO | $CO_2H$ | 3-$CH_2C_6H_5$ |
| 33 | $C_2H_3$ | $CO_2CH_3$ | $COC_3H_7$ | CO | $CO_2H$ | 3-$CH_2C_6H_5$ |
| 34 | $C_3H_7$ | $CO_2H$ | $CH_2$-2-thienyl | single bond | $CO_2H$ | 3-$CH_3$ |
| 35 | $C_4H_9$ | $CO_2CH_3$ | $CH_2$-2-furyl | single bond | $CO_2H$ | 3-$CH_3$ |
| 36 | $CH_3$ | $CO_2H$ | $CH_2$-2-furyl | NHCO | tetrazole | 3-$C_3H_7$ |
| 37 | $CH_3$ | CN | $SO_2CH_2C_6H_5$ | NHCO | tetrazole | 3-$C_3H_7$ |
| 38 | H | $CO_2H$ | $COCH_2Ph$ | NHCO | $CO_2H$ | H |
| 39 | $C_2H_5$ | $CO_2H$ | $COCH_2$-cyclohexyl | NHCO | $CO_2H$ | H |
| 40 | $CH_3$ | $CH_2N-(CH_3)_2$ | $SO_2CH_2$-2-naphthyl | $OCH_2$ | $CO_2H$ | 3-$COCH_3$ |
| 41 | $CH_3$ | $CH_2N-(C_2H_5)_2$ | $COC_6H_{13}$ | $OCH_2$ | $CO_2H$ | 3-$COCH_3$ |
| 42 | $C_2H_5$ | CN | $COC_6H_{13}$ | $OCH_2$ | $CO_2H$ | H |
| 43 | $C_2H_5$ | $CO_2H$ | $COCH(Ph)$-cyclohexyl | single bond | tetrazole | H |
| 44 | $CH_3$ | $CO_2H$ | $COCH(Ph)$-cyclohexyl | single bond | tetrazole | H |
| 45 | H | $CO_2CH_3$ | $COCH(Ph)$-cyclohexyl | single bond | tetrazole | H |
| 46 | $C_3H_7$ | $CO_2H$ | $COCH(Ph)$-cyclohexyl | single bond | tetrazole | 3-$CH_3$ |
| 47 | $C_3H_7$ | CHO | $SO_2CH_2C_6H_5$ | single bond | $NHSO_2CF_3$ | H |
| 48 | H | CN | $SO_2CH_2C_6H_5$ | NHCO | tetrazole | 3-$CH_3$ |
| 49 | $C_2H_7$ | $CO_2H$ | $COCH(Ph-4F)_2$ | single bond | tetrazole | H |
| 50 | $C_2H_7$ | $CO_2H$ | $CH_2CH(Ph)_2$ | single bond | tetrazole | H |

| Ex. | MP (°C.) |
|---|---|
| 1 | 207 |
| 2 | 124–126 |
| 27 | 267 (dec) |

Utility

We have found and characterized two distinct angiotensin II (AII) receptor subtypes by means of the discriminatory effect of dithiothreitol (DTT) and by the reciprocal selectivity of two structurally dissimilar non-peptide AII receptor antagonists.

DTT is an agent able to reduce disulfide bridges; by its disparate action on AII receptors in different tissues, DTT provided evidence of AII receptor heterogeneity. The non-peptide AII antagonists are denoted here as DuP 753 (the compound of Example 89 of EP 324377) and XB-655 (the compound of Example 13 of EP 245637 and U.S. Pat. No 4,812,462), which show reciprocal selectivity for the two subtypes. Using radioligand-receptor binding techniques, DuP 753 was found to be highly specific for an AII receptor site, designated AII receptor subtype-1 or AII-1, displaying an inhibitory constant $IC_{50}$ value of about $1.2 \times 10^{-8}$ M in rat adrenal cortex. This type of AII receptor was particularly sensitive to inactivation by DTT. XB-655 exhibited very low affinity for the AII-1 site ($IC_{50}$ value of about $3.0 \times 10^{-4}$ M), but was highly selective for a distinct AII receptor site, designated AII receptor subtype-2 or AII-2, exhibiting an inhibitory constant $IC_{50}$ value of about $1.0 \times 10^{-7}$ M in rat adrenal cortex. In contrast to the AII-1 receptor, the AII-2 receptor was resistant to DTT inactivation. Moreover, DuP 753 had very low affinity for the AII-2 receptor ($IC_{50}$ of about $1.4 \times 10^{-4}$ M). These two AII binding sites were thus shown to represent distinct subtypes of functional AII receptors. The antagonist specificity of the AII-1 and AII-2 receptor subtypes in rat adrenal cortex microsomes is summarized in Table 1. Whitebread et al. (*Biochem. Biophys. Res. Comm.* 163: 284–291 (1989)) report two AII receptor subtypes, designated A and B. DTT is reported to inhibit binding to subtype B, but to enhance binding to subtype A.

We discovered that the rat adrenal medulla and brain contain a relatively high density of AII receptors which are predominately the AII-2 subtype. XB-655 displaced the [125I]AII binding in rat brain membranes in a concentration-dependent manner yielding an $IC_{50}$ value of $3.2 \times 10^{-7}$ M. In contrast, DuP 753 displaced the binding of AII inefficiently, with an $IC_{50}$ value of $1.5 \times 10^{-4}$ M. Since the AII-2 receptor subtype is predominant in the brain, relative to the AII-1 receptor, XB-655 and related compounds should be the preferred AII receptor blockers for inhibiting adverse effects mediated by AII in the central nervous system (CNS). Such highly selective AII-2-specific antagonists will not interfere with effects mediated by the AII-1 receptor.

The distribution of AII-1 and AII-2 receptors in certain regions of the brain was determined by the binding of AII to different sections of brain slices. The results indicate that there are clusters of DTT-sensitive, DuP 753-sensitive, AII binding sites (AII-1); however, the majority of AII binding sites in the brain are DTT-insensitive, XB-655-sensitive, corresponding to AII-2 sites.

Our results show that AII binds to two distinct populations of AII receptors with similar affinity. These two receptor subtypes are not readily distinguishable by profiling with AII peptide homologs and analogs, but are identifiable by the use of the non-peptide antagonists, DuP 753 and XB-655.

The physiological and clinical relevance of the CNS renin-angiotensin system are beginning to be appreciated by the use of orally active angiotensin-converting enzyme (ACE) inhibitors. ACE inhibitors may interfere with the metabolism of other peptide hormones, such as bradykinin, substance P, neurotensin, LHRH, TRH, and vasopressin, in addition to AII. Thus, although a possible role of ACE inhibitors in enhancing cognition has been reported, it was not predictable that AII receptor antagonists would also be useful in enhancing cognitive function. Moreover, it was not known which type of non-peptide AII receptor antagonist should be used, if any, in view of the heterogeneity in antagonist specificity exhibited by AII receptor.

In light of our discovery that the brain is enriched with the AII-2 receptor subtype, we expect that non-peptide AII-2 receptor antagonists, or receptor antagonists which show affinity for both AII-1 and AII-2 receptors, may be useful for certain AII-2 induced or mediated disorders of the CNS, such as cognitive dysfunction, schizophrenic polydipsia, centrally induced hypertension, diabetic nephropathy, and excessive milk production.

The DuP 753-sensitive AII receptors have been characterized by an extensive series of non-peptide AII receptor antagonists (for example, co-assigned, co-pending U.S. Pat. application 07/279194, filed Dec. 6, 1988; European Patent application EP 0324377, published Sept. 19, 1989), in which the structure-affinity relationships observed in adrenal cortical microsomes correlate with vascular inhibitory potency and antihypertensive activity (Chiu et al. (1989) J. Pharmacol. Exp Ther. 250: 867-874; Chiu et al. (1989) Hypertension 14: 358). Thus, DuP 753 appears to be a highly specific AII blocker for the type of receptors that mediate $Ca^{+2}$-translocation. The discovery of a receptor ligand, XB-655, for the DuP 753-insensitive sites establishes the identification of a new subtype of AII receptor which is distinct from those sensitive to DuP 753. The high selectivity exhibited by each receptor antagonist towards the respective receptor subtype (3500 to 10,000-fold difference in affinity) enables us to use these blockers as pharmacological or biochemical tools for receptor identification in various target organs. A survey of receptor tissue distribution using radioligand-receptor binding techniques indicates that rat vascular tissues and liver express predominately the AII-1 receptors, while rat adrenal medulla and brain harbor primarily the AII-2 subtype. The rat adrenal cortex contains both types of receptor.

Methods and Materials

Materials

The compounds designated DuP 753 and XB-655 are synthesized according to procedures described by Carini and Duncia (European Patent application EP 0253310 and EP 0324377) in copending application U.S. Ser. No. 07/279,194, filed Dec. 6, 1988 and by Blankley et al. (European Patent Application EP 0245637, to Warner-Lambert, filed Nov. 19, 1987), respectively. Saralasin, AI, AII, AIII, and dithiothreitol (DTT) were purchased from Sigma Chemical Co. (St. Louis, MO). [$^{125}$I]AII was obtained from Du Pont-NEN Products (Boston, MA).

Radioligand-receptor binding

Procedures for the preparation of adrenal cortical microsomes and details of the binding assays are described in Chiu et al. (1989) J. Pharmacol. Exp. Ther. 250: 867-874. The same procedures and conditions were used for adrenal medullary microsomes. In brief, aliquots of a freshly prepared particulate fraction (13,000-102,000 g) were incubated with 0.05 nM [$^{125}$I]AII and varying concentrations of inhibitor in a final volume of 0.5 mL of assay buffer containing 0.25% BSA, 5 mM $MgCl_2$, and 50 mM Tris base, pH 7.2 at 25° C. After 60 min of incubation, the reaction was terminated by addition of cold assay buffer. The bound and free radioactivity were rapidly separated through glass-fiber filters, and the trapped radioactivity was determined by gamma counting. All data presented are specific binding, which is defined as that which is displaced by 1 µM unlabled AII added to the mixture.

To examine the effect of DTT on the subtypes of AII receptor, rat adrenal cortical membranes (600-20,000 g fraction) were prepared according to procedures described by Douglas et al. (1978) Endocrinol. 102: 685-696, except the above binding assay conditions were used. The membrane preparations were either treated with buffer or 5 mM DTT for 30-40 min before addition of other competing ligands.

AII receptor binding in rat smooth muscle cells and in rat brain were examined using procedures described by Chiu et al. (1989) J. Pharmacol. Exo. Ther. 250: 867-874 and by Bennett and Snyder (1976) J. Biol. Chem. 254: 7423-7430, respectively.

Autoradiaography

Fresh tissue was frozen on powdered dry ice and stored at −70° C. until used. Sections were cut at 15 microns and thaw mounted onto gelatin subbed slides. The AII binding was performed according to the procedures of Gehlert et al. (1986) Neurosic. 18: 837-856, except that the DTT was omitted from the buffer and the incubation with radioiodinated AII was 60 min. Slides were placed under X-ray film (Kodak XAR-5) and exposed for 1½ days before processing the film to produce the film autoradiograms. The slides were then fixed with paraformaldehyde vapor at 80° C. for two hours, dried under air, delipidated, and dipped in emulsion (Kodak NTB-2). The coated slides were exposed for 4-5 weeks, developed with Kodak D-19 and counter-stained with hemotoxylin-eosin to view the histology.

Identification Of The Distinct Angiotensin II Receptor Subtypes

The identification of distinct AII receptor subtypes was revealed by the use of two structurally dissimilar, non-peptide compounds, DuP 753 and XB-655, that were found to show reciprocal selectivity for the two subtypes. In the rat adrenal cortex, DuP 753 inhibited 80% of the total AII binding with an $IC_{50}$ value on the sensitive sites of about $2 \times 10^{-8}$ M, while XB-655 displaced only 20%. In the rat adrenal medulla, XB-655 gave 90% inhibition of AII binding with an $IC_{50}$ value of about $3.0 \times 10^{-8}$ M, while DuP 753 was essentially inactive as an antagonist. The combination of the two compounds completely inhibited AII binding in both tissues.

The AII receptors of adrenal cortical microsomes have been previously characterized in terms of the binding affinities of a variety of angiotensin peptides (Saltman et al. (1976) Enndocrinology 98: 894-903; Chiu et al. (1989) FASEB J. 3: A732) and non-peptide AII receptor antagonists (Chiu et al. (1989) J. Pharmacol. Exo. Ther. 250: 867-874).

Saralasin, a peptide analog of AII, is a potent and specific AII antagonist which blocks all known AII receptors, inhibits the specific binding of [$^{125}$I]AII to rat adrenal cortical microsomes in a concentration-dependent, monophasic fashion, yielding an $IC_{50}$ value of $1.0 \times 10^{-9}$ M. Complete displacement of AII was achieved at a concentration of $1 \times 10^{-7}$ M. In contrast, DuP 753 exhibited a biphasic displacement of [$^{125}$I]AII, inhibiting the specific binding of [$^{125}$I]AII in a concentration-dependent manner over a range from $10^{-9}$ M to $10^{-7}$ M. A plateau of constant binding (about 28% of the total receptor-bound AII) existed over a two-log concentration increase of DuP 753, beyond which another concentration-dependent displacement was observed. Approximated IC$_{50}$ values for these two sites were about $1.7 \times 10^{-8}$ M and $1 \times 10^{-4}$ M. These results indicate the presence of two distinct AII receptors characterized as either DuP 753-sensitive or DuP 753-insensitive.

In rat adrenal cortical microsomes, XB-655 (compound #13 of European Patent Application EP 0245637, to Warner-Lambert) inhibited only 20% of the total specific AII binding at $3 \times 10^{-5}$ M. This result was puzzling because XB-655 was reported to be an antihypertensive agent possessing high affinity for AII receptors (U.S. Pat. No. 4,812,462). On the contrary, however, we have found that this compound is inactive in antagonizing AII-induced rabbit aortic contractions at concentrations of up to $10^{-5}$ M and in lowering blood pressure in renal artery-ligated hypertensive rats at doses up to 30 mg/kg, administered IV.

We investigated whether the DuP 753-insensitive sites were sensitive to XB-655. To test this, the ligand-binding profile of the DuP 753-insensitive site was examined in the presence of a saturating concentration ($10^{-5}$ M) of DuP 753. This residual DuP 753-insensitive AII binding (expressed as 100%) was inhibited by saralasin and by XB-655, in a concentration-dependent monophasic manner, with IC$_{50}$ values of about $1.3 \times 10^{-9}$ M and $1.0 \times 10^{-7}$ M, respectively. As expected, DuP 753 inhibited the residual binding only at high concentrations, with an IC$_{50}$ value of about $1.4 \times 10^{-4}$ M.

In view of the specificity displayed by XB-655 for the DuP 753-insensitive sites, the ligand profile of DuP 753-sensitive site was reassessed in the presence of $10^{-5}$ M XB-655. Saralasin and AII inhibited the specific binding as expected with IC$_{50}$ values of about 1.7 and $2.3 \times 10^{-9}$, respectively. In contrast to the result in the absence of XB-655, DuP 753 now displayed a concentration dependent monophasic inhibition, eliminating essentially all AII binding, with an IC$_{50}$ of about $1.2 \times 10^{-8}$ M. As expected, XB-655 was rather inactive under this condition, inhibiting the binding only at very high concentrations, with an IC$_{50}$ of about $3.0 \times 10^{-4}$ M.

The selectivity of each ligand for its respective receptor is presented as a ratio between the IC$_{50}$ obtained for the DuP 753-sensitive sites (AII-1) over that for the XB-655-sensitive sites (AII-2). The results show that DuP 753 is about 10,000-fold more selective for the AII-1 receptors, whereas XB-655 has about 3500-fold higher affinity for AII-2 receptors. In contrast, the peptide agonist (AII) and antagonist (saralasin) exhibit no preference for one AII receptor subtype relative to the other subtype. The antagonist specifity of the AII-1 and AII-2 receptor subtypes in rat adrenal cortex microsomes is summarized in Table 2.

TABLE 2

Antagonist Specificity Exhibited by AII Receptor Subtypes

| Compound | IC$_{50}$ (M) AII-1 | AII-2 |
|---|---|---|
| AII | $2.3 \times 10^{-9}$ | $9.0 \times 10^{-10}$ |
| Saralasin | $1.7 \times 10^{-9}$ | $1.3 \times 10^{-9}$ |
| Example 2 | $1.2 \times 10^{-5}$ | $1.4 \times 10^{-8}$ |
| Example 27 | $3.0 \times 10^{-4}$ | $1.0 \times 10^{-8}$ |
| DuP 753 | $1.2 \times 10^{-8}$ | $1.4 \times 10^{-4}$ |
| XB-655 | $3.0 \times 10^{-4}$ | $1.0 \times 10^{-7}$ |

AII-1 site binding was determined in the presence of $10^{-5}$ M XB-655. AII-2 site binding was determined in the presence of $10^{-5}$ M DuP 753. IC$_{50}$ was determined by displacement of [$^{125}$I]AII from the receptor by the indicated compound. The compounds of this application, designated Example 2 and Example 27, are seen to bind selectively to AII-2 receptors. These compounds are expected to be useful in disease states mediated by AII-2 receptors and responsive to blockers of the AII-2 receptor, including CNS disorders.

Distribution of AII Receptor Subtypes

Autoradiographic examination of [$^{125}$I]AII binding to the rat adrenal gland was undertaken to explore the localization of AII receptors and possible anatomical differentiation of subtypes. [$^{125}$I]AII densely labeled the outer layers of the adrenal cortex as well as the entire adrenal medulla, as reported by Catt et al. (1984) *J. Cardiovasc. Pharmacol.* 6: S575–S586. Most of the cortical labeling appeared to be over the zona glomerulosa with moderate labeling of zona fasciculata. Unlabeled AII potently inhibited the labeling in both cortex and medulla. In the presence of $10^{-5}$ M DuP 753, the labeling over the cortex was significantly reduced and the resistant sites were found to be distributed uniformly around the outer layer of the cortex. The labeling of the adrenal medulla, however, was not appreciably affected by DuP 753. By contrast, $10^{-6}$ M XB-655 had no apparent effect on cortical labeling, but almost totally eliminated the labeling of the medulla. When both compounds were applied in combination, the AII labeling of both regions was completely abolished.

The results show that DuP 753-resistant AII-2 receptor sites are present in the cortical zona glomerulosa and predominate in the medulla of the rat adrenal gland. To characterize these AII receptors further, [$^{125}$I]AII specific binding to rat adrenal medullary microsomes was studied. Saralasin inhibited the binding in a concentration-dependent fashion with an IC$_{50}$ value of $4 \times 10^{-10}$ M. About 90% of the total binding was resistant to displacement by DuP 753 which is consistent with the results obtained by autoradiographic techniques. In contrast, the inhibition by XB-655 was concentration-dependent and nearly monophasic, yielding an IC$_{50}$ value of $3 \times 10^{-8}$ M. Interestingly, 10% of the binding was resistant to XB-655, which complements the 10% inhibition seen with DuP 753 below $1 \times 10^{-5}$ M.

The present studies using radioligand binding and autoradiographic techniques clearly demonstrate the existence of two subtypes of AII receptors in the rat adrenal gland. The adrenal cortex, particularly the zona glomerulosa, contains predominately the DuP 753-sensitive AII-1 receptor, whereas the medulla harbors almost exclusively the DuP 753-insensitive, XB-655-sensitive type of AII receptor (AII-2). Rat aortic smooth muscle cells were found to display primarily the DuP 753-sensitive AII binding sites (AII-1), in contrast to the rat adrenal medulla and brain, which are dominated by DuP 753-insensitive, XB-655-sensitive AII binding sites (AII-2).

Discrimination of AII Receptor Subtype by DTT Sensitivity

The following studies were designed to examine whether DTT could differentiate the AII-1 and AII-2 subtypes of AII receptor. The differential effect of DTT on AII receptors in rat liver was previously reported by Gunther et al. (1984) *J. Biol. Chem.* 259: 7622–7629. AII receptors obtained from a 600-20,000 g fraction of adrenal cortical membranes were pretreated with and without 5 mM DTT for 30 min at room temperature before addition of ligands.

The inhibitory potency of AII was enhanced 2.5-fold in the presence of DTT, with an $IC_{50}$ of $1 \times 10^{-9}$ M in the absence of DTT and an $IC_{50}$ of $0.4 \times 10^{-9}$ M in the presence of DTT. Saralasin inhibition was not significantly altered by DTT. In contrast, the inhibitory effect of DuP 753 at concentrations between $3 \times 10^{-9}$ to $3 \times 10^{-6}$ M was essentially abolished in the presence of DTT. On the other hand, DTT transformed XB-655 from a weak to a potent inhibitor, displacing the binding in a concentration-dependent and nearly monophasic fashion, yielding an apparent $IC_{50}$ value of $2.5 \times 10^{-7}$ M. Thus, the DTT-insensitive site shows very low affinity for DuP 753. These data indicate that the DuP 753-sensitive receptors (AII-1) are inactivated by DTT and the remaining DTT-resistant sites are the XB-655-sensitive AII-2 receptors.

Dosage Forms

The compounds of this invention can be administered for the treatment of AII-2 mediated CNS disorders and other AII-2 receptor mediated disorders by any route and dosage form that effects contact of the active ingredient compound with the site of action in the body of a warm-blooded animal. For example, administration can be parenteral, i.e., subcutaneous, intravenous, intramuscular, or intraperitoneal. Alternatively, or concurrently, in some cases administration can be by the oral route, or topically, e.g., for the treatment of glaucoma.

The compounds can be administered by any conventional means available for use with pharmaceuticals, either as individual therapeutic agents or as part of a combination of therapeutic agents. They can be administered alone, but are generally administered with a pharmaceutical carrier selected on the basis of the chosen route of administration and standard pharmaceutical practice.

Reference to the compounds of this invention includes pharmaceutically acceptable acid addition salts, base salts, and N-oxide derivatives thereof. By the term "pharmaceutically acceptable acid addition salt" is meant any non-toxic pharmaceutically suitable salt of a compound described above which has the desired pharmacological properties in mammals. Preparation of such salts is well know to those skilled in the pharmaceutical sciences. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate, and pamoate. Methods for preparation of N-oxide derivatives are also well known in the art. Examples of inorganic bases suitable for the formation of compounds of this invention include, e.g., the hydroxides, carbonates, and bicarbonates of ammonia, sodium, lithium, potassium, calcium, magnesium, aluminum, and zinc. Pharmaceutically acceptable base addition salts of the compounds of the invention may also be formed with suitable organic bases that are nontoxic and strong enough to form such salts, as is readily understood by those of ordinary skill in the art. See, e.g., "Pharmaceutical Salts", *J. Pharm. Sci.* 66 (1): 1-19 (1977).

For the purpose of this disclosure, a warm-blooded animal is a member of the animal kingdom possessed of a homeostatic mechanism, preferably a mammal.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water for injection, a suitable oil, saline, aqueous dextrose (glucose), and related sugar solutions and glycols such as propylene glycol or polyethylene glycols are suitable carriers for parenteral solutions. Solutions for parenteral administration must be sterile and nonpyrogenic and will preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Information about suitable pharmaceutical carriers and formulations may be found, e.g., in various editions of *Remington's Pharmaceutical Sciences*, Mack Publishing Company, or of the USP/NF.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets is prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injection

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered in conjunction with another therapeutic agent. When the drugs are administered in physical combination, the dosage form and administration route should be selected for compatibility with both drugs.

We claim:

1. A compound of the formula:

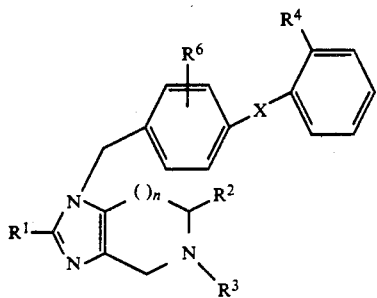

or a pharmaceutically acceptable salt thereof; wherein
(1) $R^1$ is:
   (a) H,
   (b) halo,
   (c) $C_1-C_6$ alkyl, or $C_3-C_6$ alkenyl or alkynyl,
   (d) $R^{14}$—$(CH_2)_x$—wherein x is one, two, three, four or five, and $R^{14}$ is $C_3-C_8$ cycloalky,, naphthyl, [heteroaryl,] 2-, 3-, or 4-pyridyl; 1-, 2-, or 4-imidazolyl; 1-, 2-, 3-, 4-, 5-, 6- or 7-indolyl; 2-, or 3-pyraxolyl, phenyl unsubstituted or substituted with from one through five substituents comprising $C_1-C_4$ alkyl, halo, trifluoromethyl, hydroxy, $C_1-C_4$ akloxy, lower acyloxy, amino, N-lower monoalkylamino, N,N-lower dialkylamino, lower thioalkyl, lower alkylsulfonyl, nitro or —NHCOR$^{10}$ wherein R$^{10}$ is lower alkyl, phenyl unsubstituted or substituted with lower alkyl, or —NHR$^{11}$ wherein R$^{11}$ is H or $C_1-C_4$ alkyl,
   (e)

wherein $R^{14}$ is independently as defined above, or (f) $R^{14}$—CH(OH)—wherein $R^{14}$ is independently as defined above;
(2) $R^2$ is
   (a) —$(CH_2)_x$ OR$^7$ wherein R$^7$ is H, $C_1-C_4$ aklyl, $C_1-C_4$ acyl, $C_3-C_6$ cycloalkyl, phenyl, or bensyl,
   (b) —$(CH_2)_x$NR$^7$R$^8$ wherein R$^7$ is independently as defined above and R$^8$ is H, $C_1-C_4$ alkyl, phenyl, benzyl, or $C_1-C_4$ acyl,
   (c) —$(CH_2)_x$OC$_5$H$_{11}$,
   (d) —CHO
   (e) —CN,
   (f) —COOR$^9$ wherein R$^9$ is hydrogen, $C_1-C_4$ alkyl or benzyl; unsubstituted or substituted with from one through five substituents, comprising alkyl, halo, trifluoromethyl, amino, N-lower monoaklylamino, N,N-lower dialkylamino, lower thioaklyl, lower alkylsulfonyul, OH, or $C_1-C_4$ alkoxy, or nitro.
   (iii) —(CH=CR$^{12}$)—R$^{16}$, is hydrogen or lower alkyl and R$^{16}$ is
      (a) alkyl of from four to twenty carbons, inclusive,

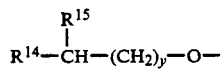

(b) wherein y, R$^{14}$ and R$^{15}$ are, independently, as defined above, and
   (iv) R$^{14}$(CH$^2$)$_y$R$^{14}$ and R$^{12}$ are, independently, as defined above,
   (v) R$^{14}$—(CH$_2$)$_y$—O—wherein y and R$^{14}$ are independently as defined above,
   (vi)

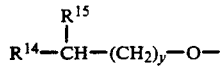

wherein R$^{14}$, R$^{15}$, and y are independently as defined above,
   (d) SO$_2$R$^5$ wherein R$^5$ is, independently, as defined above;
(4) R$^4$ is —CO$_2$H, —NHSO$_2$CF$_3$, or

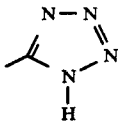

2. A compound of claim 1 wherein:

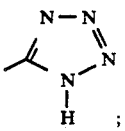

1-3 substituents selected from $C_1-C_4$ aklyl, halo, CF$_3$, OH, $C_1-C_4$ alkoxy, N-lower monoalkylamino, N,N-lower dialkylamino, NO$_2$;
X is a carbon-carbon single bond, —NHCO—, —OCH$_2$—, —O—, or —CO—;
n=1-2.

3. A compound of claim 1 wherein:
R$^3$ is —COR$^5$:

$R^5$ is $-(CH_2)_yCHR^{14}R^{15}$.

4. A compound of claim 3 wherein:
$R^3$ is $COR^5$;
$R^5$ is $-(CH_2)_yCHR^{14}R^{15}$;
$R^{14}$ is $C_3-C_8$ cycloalkyl, naphthyl, pyridyl, furyl, thienyl, phenyl unsubstituted or substituted with 1-3 substitutents selected from $C-C_4$ aklyl, halogen, $CF_3$, OH;
$R^{15}$ is H, $C_1-C_4$ alkyl, $C_3-C_8$ cycloalkyl, naphthyl, phenyl optionally substituted with 1-3 substitutents selected from $C_1-C_4$ aklyl, halogen, $CF_3$, OH, $C_1-C_4$ alkoxy, N-lower monoalkylamino, N,N, lower dialkylamino, $NO_2$.

5. A compound of claim 1 which is methyl-5-diphenylacetyl-4,5,6,7-tetrahydro-1H-imidazo-(4,5-C)-pyridine-6-carboxylic acid, 1-5-bis-phenylacetyl-4,5,6,7-tetrahydro-1H-imidazo 4,5-pyridine-6-carboxylic acid or a pharmaceutically acceptable salt thereof.

6. A compound of claim 1 which is methyl-5-diphenylacetyl-4,5,6,7-tetrahydro-1H-imidazo (4,5-C)-pyridine-6-carboxylate, 1-[4-(2-carboxyphenyl-carbonylamino)-3-methyl-phenylmethyl]5-bis-phenylacetyl-4,5,6,7-tetrahydro-1H-imidazo pyridine-6-carboxylic monomethyl ester acid or a pharmaceutically accpetable salt thereof. pyridine-6-carboxylate, or a pharmaceutically acceptable salt thereof.

7. A pharmaceutical composition comprising a suitable pharmaceutical carrier and a therapeutically effective amount of a compound of claim 1.

8. A pharmaceutical composition comprising a suitable pharmaceutical carrier and a therapeutically effective amount of a compound of claim 2.

9. A pharmaceutical composition comprising a suitable pharmaceutical carrier and a therapeutically effective amount of a compound of claim 3.

10. A pharmaceutical composition comprising a suitable pharmaceutical carrier and a therapeutically effective amount of a compound of claim 4.

11. A pharmaceutical composition comprising a suitable pharmaceutical carrier and a therapeutically effective amount of the compound of claim 5.

12. A pharmaceutical composition comprising a suitable pharmaceutical carrier and a therapeutically effective amount of the compound of claim 6.

13. A method for the treatment of a disorder or a condition in a mammal mediated by AII-2 receptors comprising administering to the mammal a therapeutically effective amount of a compound of claim 1.

14. A method for the treatment of a disorder or a condition in a mammal mediated by AII-2 receptors comprising administering to the mammal a therapeutically effective amount of a compound of claim 2.

15. A method for the treatment of a disorder or a condition in a mammal mediated by AII-2 receptors comprising administering to the mammal a therapeutically effective amount of a compound of claim 3.

16. A method for the treatment of a disorder or a condition in a mammal mediated by AII-2 receptors comprising administering to the mammal a therapeutically effective amount of a compound of claim 4.

17. A method for the treatment of a disorder or a condition in a mammal mediated by AII-2 receptors comprising administering to the mammal a therapeutically effective amount of the compound of claim 5.

18. A method for the treatment of a disorder or a condition in a mammal mediated by AII-2 receptors comprising administering to the mammal a therapeutically effective amount of the compound of claim 6.

19. A method for the treatment of cognitive or neurological dysfunction mediated by AII in a mammal comprising administering to the mammal a therapeutically effective amount of a compound of claim 1

20. A method for the treatment of cognitive or neurological dysfunction mediated by AII in a mammal comprising administering to the mammal a therapeutically effective amount of a compound of claim 2.

21. A method for the treatment of cognitive or neurological dysfunction mediated by AII in a mammal comprising administering to the mammal a therapeutically effective amount of a compound of claim 3.

22. A method for the treatment of cognitive or neurological dysfunction mediated by AII in a mammal comprising administering to the mammal a therapeutically effective amount of a compound of claim 4.

23. A method for the treatment of cognitive or neurological dysfunction mediated by AII in a mammal comprising administering to the mammal a therapeutically effective amount of the compound of claim 5.

24. A method for the treatment of cognitive or neurological dysfunction mediated by AII in a mammal comprising administering to the mammal a therapeutically effective amount of the compound of claim 6.

* * * * *